(12) United States Patent
Ebenbeck et al.

(10) Patent No.: US 7,528,146 B2
(45) Date of Patent: May 5, 2009

(54) SUBSTITUTED 1H-PYRROLO[2,3-B]PYRIDINES AND PREPARATION THEREOF

(75) Inventors: Wolfgang Ebenbeck, Leverkusen (DE); Perez Santiago Figueroa, Leverkusen (DE); Hartmut Schirok, Wuppertal (DE)

(73) Assignee: LANXESS Deutschland GmbH, Leverkusen (DE)

( * ) Notice: Subject to any disclaimer, the term of this patent is extended or adjusted under 35 U.S.C. 154(b) by 183 days.

(21) Appl. No.: 11/298,437

(22) Filed: Dec. 9, 2005

(65) Prior Publication Data

US 2006/0128661 A1    Jun. 15, 2006

(30) Foreign Application Priority Data

Dec. 15, 2004  (DE)  ........................ 10 2004 060 659

(51) Int. Cl.
C07D 471/02 (2006.01)
A61K 31/4353 (2006.01)
(52) U.S. Cl. ...................................... 514/300; 546/113
(58) Field of Classification Search .................. None
See application file for complete search history.

(56) References Cited

U.S. PATENT DOCUMENTS 5,700,809 A * 12/1997 Leeson et al. ............... 514/300
5,977,131 A * 11/1999 Nagel ........................... 514/300

FOREIGN PATENT DOCUMENTS

WO  WO 03/082289  10/2003
WO  WO 2004/009601  1/2004
WO  WO 2004/016609  2/2004
WO  WO 2004/039796  5/2004
WO  WO 2005/108397  11/2005

OTHER PUBLICATIONS

Sanchez-Obregon et al., Canadian Journal of Chemistry, 1992, vol. 70, pp. 1531-1536.*
http://www.cem.msu.edu/~reusch/VirtTxtJml/alhalrx1.htm, 2009.*
Greene T. W., Wuts P. G. W. in Protective Groups in Organic Synthesis; John Wiley & Sons, Inc. 1999, Protection for Imidazoles, Pyrazoles, Indoles, and other aromatic heterocycles, p. 615-631.
M. A. McClinton, Tetrahedron, 1992, 6565-6584.
Wang C. L. J., Org. React, 34, 319-400.
Hudlicky, M., Org. React. 35, 513-637.
J. Amer. Chem. Soc. 1956, 78, 1247-1249.

* cited by examiner

*Primary Examiner*—Zinna N Davis
(74) *Attorney, Agent, or Firm*—Michael A. Miller

(57) ABSTRACT

The invention relates to novel substituted 1H-pyrrolo[2,3-b] pyridines of the general formula (I)

(I)

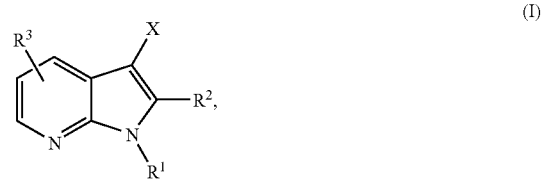

to processes for their preparation and to intermediates therefor.

13 Claims, No Drawings

SUBSTITUTED 1H-PYRROLO[2,3-B]PYRIDINES AND PREPARATION THEREOF

The invention relates to novel substituted 1H-pyrrolo[2,3-b]pyridines, to processes for their preparation and to intermediates therefor.

1H-Pyrrolo[2,3-b]pyridines are important intermediates for the preparation of active pharmaceutical ingredients (cf. WO-A 2004/009601 or WO-A 2004/039796). Moreover, substituted 1H-pyrrolo[2,3-b]pyridines and related compounds may themselves have pharmaceutical activity and be used as active ingredients in pharmaceutical compositions (cf. WO-A 03/082289, WO-A 2004/016609 and WO-A 2004/009601). For example, WO-A 2004/016609 describes the use of substituted 1H-pyrrolo[2,3-b]pyridines as inhibitors of kinase Itk, WO-A 2004/009601 the use of active ingredients which contain a 1H-pyrrolo[2,3-b]pyridine fragment as tyrosine kinase activity inhibitors of growth receptors, which is why they are suitable for use as anticancer drugs, and WO-A 03/082289 describes the possibility of using substituted 1H-pyrrolo[2,3-b]pyridines for the treatment of HIV and AIDS owing to their antiviral action.

Owing to the variety of potential action of 1H-pyrrolo[2,3-b]pyridines or compounds containing 1H-pyrrolo[2,3-b]pyridine units, there is still a need for further such substituted 1H-pyrrolo[2,3-b]pyridines which are suitable, for example, for the preparation of active pharmaceutical ingredients or as active ingredients themselves for the treatment of other diseases, or which are superior to the known compounds, for example with regard to solubility, efficacy or pharmacokinetics.

It is thus an object of the present invention to discover such novel substituted 1H-pyrrolo[2,3-b]pyridines.

This object is achieved by the preparation of the inventive compounds of the general formula (I). None of these compounds has hitherto been described in the prior art.

The present invention thus provides compounds of the general formula (I)

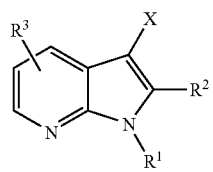

(I)

in which $R^1$ is H or optionally substituted linear, branched or cyclic $C_1$-$C_{18}$-alkyl, preferably $C_1$-$C_6$-alkyl and $C_3$-$C_6$-cycloalkyl, $C_1$-$C_{18}$-alkoxy, preferably $C_1$-$C_6$-alkoxy, $C_2$-$C_6$-alkenyl, $C_4$-$C_6$-cycloalkenyl, $C_2$-$C_6$-alkynyl, $C_4$-$C_{24}$-aryl, preferably $C_6$-$C_{24}$-aryl, $C_5$-$C_{18}$-arylalkyl, $C_5$-$C_{18}$-aryloxy, $C_5$-$C_{18}$-arylalkoxy, —$SO_2R^x$, —$SO_2NR^xR^y$, —$C(O)OR^x$ or —$C(O)NR^xR^y$, tri-$C_1$-$C_{18}$-alkylsilyl groups and also further suitable NH protecting groups for aromatic compounds, in which $R^x$ and $R^y$ are each independently H or optionally substituted linear, branched or cyclic $C_1$-$C_{18}$-alkyl, preferably $C_1$-$C_6$-alkyl and $C_3$-$C_6$-cycloalkyl, $C_1$-$C_{18}$-alkoxy, preferably $C_1$-$C_6$-alkoxy, $C_2$-$C_6$-alkenyl, $C_4$-$C_6$-cycloalkenyl, $C_2$-$C_6$-alkynyl, $C_4$-$C_{24}$-aryl, preferably $C_6$-$C_{24}$-aryl, $C_5$-$C_{18}$-arylalkyl, $C_5$-$C_{18}$-aryloxy or $C_5$-$C_{18}$-arylalkoxy, $R^2$, $R^3$ are each independently H, Cl, F, Br, $NO_2$, pseudohalogen, formyl or protected formyl, carboxyl, $C(S)NH_2$, $C(O)NH_2$, optionally substituted linear, branched or cyclic $C_1$-$C_{18}$-alkyl, preferably $C_1$-$C_6$-alkyl and $C_3$-$C_6$-cycloalkyl, $C_1$-$C_{18}$-fluoroalkyl, preferably $C_1$-$C_6$-fluoroalkyl, $C_1$-$C_{18}$-alkoxy, preferably $C_1$-$C_6$-alkoxy, $C_1$-$C_{18}$-fluoroalkoxy, preferably $C_1$-$C_6$-fluoroalkoxy, $C_2$-$C_6$-alkenyl, $C_4$-$C_6$-cycloalkenyl, $C_2$-$C_6$-alkynyl, $C_4$-$C_{24}$-aryl, preferably $C_6$-$C_{24}$-aryl, $C_5$-$C_{18}$-arylalkyl or $C_5$-$C_{18}$-arylalkoxy, where, in the case that $R^3$ is $C_5$-$C_{18}$-arylalkyl and it is bonded via the alkyl moiety of the $C_5$-$C_{18}$-arylalkyl radical to the pyridine ring, this alkyl moiety has at least two carbon atoms between aryl moiety of the $C_5$-$C_{18}$-arylalkyl radical and pyridine ring, and X is $C_1$-$C_{18}$-fluoroalkyl, preferably $C_1$-$C_6$-fluoroalkyl.

The present invention likewise provides salts of the compound of the general formula (I).

Further suitable NH protecting groups in aromatic compounds which are possible for $R^1$ are known to those skilled in the art, for example, from Greene T. W., Wuts P. G. W. in Protective Groups in Organic Synthesis; John Wiley & Sons, Inc. 1999, Protection for Imidazoles, Pyrazoles, Indoles, and other aromatic heterocycles, p. 615-631.

Examples of the suitable radicals for $R^1$ listed above include the following: in the context of the invention, —C(O)$OR^x$ or —C(O)$NR^xR^y$ may, for example, be carbamates or oxycarbonyl groups, for example optionally substituted $C_1$-$C_{18}$-alkoxycarbonyl, tri-$C_1$-$C_{18}$-alkysiloxycarbonyl, $C_3$-$C_6$-cycloalkoxycarbonyl groups, in particular 2,2,2-trichloroethoxycarbonyl, 2-(trimethylsilyl)ethoxycarbonyl, tert-butoxycarbonyl, 2,4-dimethylpent-3-yloxycarbonyl, cyclohexyloxycarbonyl, 1,1-dimethyl-2,2,2-trichloroethoxycarbonyl, adamantyloxycarbonyl groups; —$SO_2R^x$ or —$SO_2NR^xR^y$ may, for example, be optionally substituted N,N-di-$C_1$-$C_{18}$-alkylsulphonyl, $C_4$-$C_{24}$-arylsulphonyl groups, in particular o-, m-, p-toluenesulphonyl, phenylsulphonyl, p-methoxyphenylsulphonyl, mesitylenesulphonyl, N,N-dimethylsulphonyl groups; optionally substituted $C_1$-$C_{18}$alkyl or $C_4$-$C_{24}$-aryl groups may, for example, be vinyl, 2-chloroethyl, 1-ethoxyethyl, 2-(2'-pyridyl)ethyl, 2-(4-nitrophenyl)ethyl groups and allyl, benzyl, p-methoxybenzyl, 3,4-dimethoxybenzyl, 3-methoxy- or 3,5-dimethoxybenzyl, 2-nitrobenzyl, 2,4-dinitrophenyl, phenacyl, triphenylmethyl groups; optionally substituted tri-$C_1$-$C_{18}$-alkylsilyl groups may, for example, be t-butyldimethylsilyl, triisopropylsilyl groups; optionally substituted $C_1$-$C_{18}$-alkyl groups may, for example, also be dimethylaminoethyl groups; optionally substituted $C_3$-$C_6$-cycloalkyl groups may, for example, be 2-tetrahydropyranyl groups; optionally substituted $C_1$-$C_{18}$-alkoxy groups may, for example, be methoxymethyl, diethoxymethyl, 2-chloroethoxymethyl, 2-(trimethylsilyl)ethoxymethyl, t-butoxymethyl, t-butyldimethylsiloxymethyl, pivaloyloxymethyl groups; optionally substituted $C_3$-$C_6$-cycloalkoxy, benzyloxymethyl groups and optionally substituted $C_1$-$C_{18}$-alkylamides, $C_4$-$C_{24}$-arylamides or $C_5$-$C_{18}$-arylalkylamindes may, for example, be hydroxycarbonyl, formyl, N,N-dimethylaminocarbonyl, dichloromethylcarbonyl, t-butylcarbonyl, diphenylthiophosphine groups. The above list serves to illustrate by way of example and is not to be regarded as exclusive.

The present invention preferably provides compounds of the general formula (I) in which $R^1$ is H, —$SO_2R^x$, —$SO_2NR^xR^y$, —C(O)$OR^x$ or —C(O)$NR^xR^y$, where $R^x$ and $R^y$ are each independently H or optionally substituted $C_1$-$C_{18}$-alkyl, $C_4$-$C_{24}$-aryl or $C_5$-$C_{18}$-arylalkyl, and $R^1$ is preferably H, o-, m-, p-toluenesulphonyl or t-butyloxycarbonyl. In preferred embodiments, $R^1$ is —$SO_2R^x$ or —C(O)

OR$^x$, in which R$^x$ is optionally substituted C$_1$-C$_{18}$-alkyl, C$_4$-C$_{24}$-aryl or C$_5$-C$_{18}$-arylalkyl, preferably p-toluenesulphonyl or t-butyloxycarbonyl.

The present invention preferably further provides compounds of the general formula (I) in which R$^2$ is H, C$_1$-C$_6$-alkyl, C$_6$-C$_{24}$-aryl or C$_5$-C$_{18}$-arylalkyl.

The present invention preferably further provides compounds of the general formula (I) in which R$^3$ is H, Cl, F, Br, NO$_2$, CN, formyl or protected formyl, C$_1$-C$_6$-alkyl, C$_1$-C$_6$-fluoroalkyl, C$_1$-C$_6$-alkoxy, C$_1$-C$_6$-fluoroalkoxy, C$_6$-C$_{24}$-aryl, C$_5$-C$_{18}$-arylalkyl, C$_5$-C$_{18}$-arylalkoxy, preferably H or Cl.

The present invention preferably further provides compounds of the general formula (I) in which X is C$_1$-C$_6$-fluoroalkyl, preferably CF$_3$, CF$_2$CF$_3$ or CF(CF$_3$)$_2$, more preferably CF$_3$.

Mixtures comprising one or more of the above-specified compound(s) of the general formula (I) also form part of the subject-matter of the present invention.

Depending on the definition of R$^1$, R$^2$ or R$^3$, the compounds of the general formula (I) may occur in enantiomeric or diastereomeric forms. The invention encompasses all enantiomers, diastereomers, racemates, mixtures of enantiomers or diastereomers in any molar ratios.

In addition, depending on the definition of R$^1$, R$^2$ or R$^3$, the compounds of the general formula (I) may occur in different tautomeric forms. The invention likewise encompasses all possible tautomeric forms and mixtures thereof in any molar ratios.

Salts of the inventive compounds may be physiologically acceptable salts of the inventive compounds of the general formula (I) with inorganic or organic acids. Preference is given to salts with inorganic acids, for example hydrochloric acid, hydrobromic acid, phosphoric acid or sulphuric acid, or salts with organic carboxylic or sulphonic acids, for example acetic acid, trifluoroacetic acid, propionic acid, maleic acid, fumaric acid, malic acid, citric acid, tartaric acid, lactic acid, benzoic acid or methanesulphonic acid, ethanesulphonic acid, benzenesulphonic acid, toluenesulphonic acid or napthalenesulphonic acid.

Depending on the definition of R$^1$, R$^2$ or R$^3$, salts of the inventive compounds may likewise be physiologically acceptable salts of the inventive compounds of the general formula (I) with customary bases, for example alkali metal salts, e.g. sodium or potassium salts, alkaline earth metal salts, e.g. calcium or magnesium salts, ammonium salts derived from ammonia or organic amines, for example diethylamine, triethylamine, ethyldiisopropylamine, procaine, dibenzylamine, N-methylmorpholine, dihydroabietylamine or methylpiperidine, or salts of ethanolamines, for example 2-diethylaminoethanol, 2-[(2-hydroxyethyl)methylamino]ethanol.

Alkyl, alkenyl, alkynyl or alkoxy are in each case independently a linear, cyclic, branched or unbranched alkyl, alkenyl, alkynyl or alkoxy radical. The same applies to the non-aromatic moiety of an arylalkyl radical, and to alkyl, alkylene or alkoxy constituents of more complex substituents, for example alkylsulphonyl, alkyloxycarbonyl, etc.

C$_1$-C$_6$-Alkyl is, for example, methyl, ethyl, n-propyl, isopropyl, n-butyl, sec-butyl, tert-butyl, n-pentyl, 1-methylbutyl, 2-methylbutyl, 3-methylbutyl, neo-pentyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl or 1-ethyl-2-methylpropyl, and C$_1$-C$_{18}$-alkyl is additionally, for example, n-heptyl and n-octyl, pinacoyl, adamantyl, the isomeric menthyls, n-nonyl, n-decyl, n-dodecyl, n-tridecyl, n-tetradecyl, n-hexadecyl or n-octadecyl.

C$_3$-C$_6$-Cycloalkyl is, for example, cyclopropyl, cyclobutyl, cyclopentyl or cyclohexyl.

C$_1$-C$_6$-Alkoxy is, for example, the alkoxy groups corresponding to the above alkyl groups, for example methoxy, ethoxy, n-propoxy, iso-propoxy, n-butoxy, sec-butoxy, tert-butoxy, etc. C$_1$-C$_{18}$-Alkoxy is also, for example, the alkoxy groups corresponding to the above alkyl groups.

C$_1$-C$_6$-Fluoroalkyl and C$_1$-C$_{18}$-fluoroalkyl are, for example, the part-fluorinated or perfluorinated alkyl groups corresponding to the above alkyl groups. C$_1$-C$_6$-Fluoroalkoxy and C$_1$-C$_{18}$-fluoroalkoxy are, for example, the part-fluorinated or perfluorinated alkoxy groups corresponding to the above alkoxy groups.

C$_2$-C$_6$-Alkenyl is, for example, the alkenyl groups corresponding to the above alkyl groups, for example ethenyl, propenyl, butenyl, pentenyl or hexenyl. C$_2$-C$_6$-Alkynyl is, for example, the alkynyl groups corresponding to the above alkyl groups, for example ethynyl, propynyl, butynyl, pentynyl or hexynyl. C$_4$-C$_6$-Cycloalkyl is, for example, cyclobutenyl, cyclopentenyl or cyclohexenyl.

Aryl is in each case independently an aromatic radical having 4 to 24 skeleton carbon atoms, in which no, one, two or three skeleton carbon atoms per cycle, but at least one skeleton carbon atom in the entire molecule, may be substituted by heteroatoms selected from the group of nitrogen, sulphur or oxygen, but is preferably a carbocyclic aromatic radical having 6 to 24 skeleton carbon atoms. The same applies to the aromatic moiety of an arylalkyl radical, and to aryl constituents of more complex substituents, for example arylsulphonyl, aryloxycarbonyl.

Examples of C$_6$-C$_{24}$-aryl are phenyl, o-, p-, m-tolyl, naphthyl, phenanthrenyl, anthracenyl or fluorenyl; examples of heteroaromatics C$_4$-C$_{24}$-aryl in which no, one, two or three skeleton carbon atoms per cycle, but at least one skeleton carbon atom in the entire molecule, may be substituted by heteroatoms selected from the group of nitrogen, sulphur or oxygen are pyridyl, pyridyl N-oxide, pyrimidyl, pyridazinyl, pyrazinyl, thienyl, furyl, pyrrolyl, pyrazolyl, imidazolyl, thiazolyl, oxazolyl or isoxazolyl, indolizinyl, indolyl, benzo[b]thienyl, benzo[b]furyl, indazolyl, quinolyl, isoquinolyl, naphthyridinyl, quinazolinyl, benzofuranyl or dibenzofuranyl.

Arylalkyl is in each case independently a straight-chain, cyclic, branched or unbranched alkyl radical as defined above, which may be substituted singly, multiply or fully by aryl radicals as defined above.

C$_5$-C$_{18}$-Arylalkyl is, for example, benzyl or (R)— or (S)-1-phenylethyl.

Halogen may be fluorine, chlorine, bromine or iodine. Pseudohalogen may, for example, be cyanide, cyanate or thiocyanate.

In the context of the invention, all radical definitions, parameters and illustrations above and listed below, in general or within areas of preference, may be combined with one another, i.e. also between particular areas and areas of preference in any desired manner.

Possible substituents for the R$^1$ to R$^3$ radicals include numerous organic groups, for example alkyl, cycloalkyl, aryl, halogen, hydroxyl, ether, thioether, disulphide, sulphoxide, sulphonic acid, sulphonate, protected amino, aldehyde, keto, carboxylic ester, carbonate, carboxylate, cyano, alkylsilane and alkoxysilane groups, and also optionally protected carboxylamide groups. In the case that R$^3$ is an aryl-substituted $C_1$-$C_{18}$-alkyl radical, this alkyl radical has to have at least two carbon atoms between aryl substituents and pyridine ring.

Examples of compounds of the general formula (I) include the following compounds of the formulae (I-1) to (I-4):

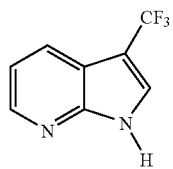
(I-1)

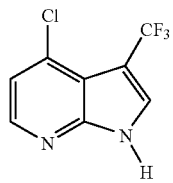
(I-2)

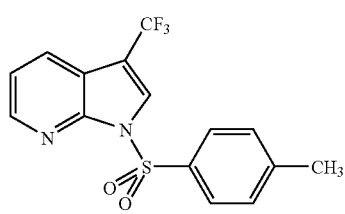
(I-3)

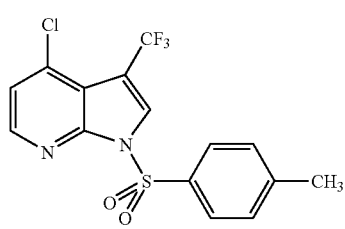
(I-4)

The inventive compounds of the general formula (I) can be prepared in a simple manner by various routes.

For example, the compounds of the general formula (I) may be prepared from compounds of the general formula (II)

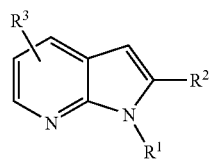
(II)

in which $R^1$, $R^2$ and $R^3$ are each as defined for the general formula (I), by converting the compounds of the general formula (II) first by means of halogenation to compounds of the general formula (VI)

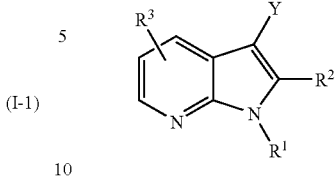
(VI)

in which Y is halogen, and subsequently converting them using a fluoroalkylating agent to compounds of the general formula (I) in which X is $C_1$-$C_{18}$-fluoroalkyl. The principle of such reactions with fluoroalkylating agent is described, for example, in M. A. McClinton, Tetrahedron, 1992, 6565-6584.

The present invention thus further provides a process for preparing the inventive compounds of the general formula (I)

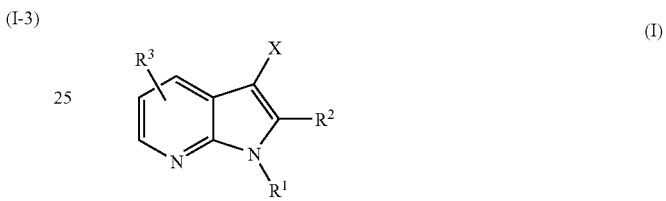
(I)

in which X is $C_1$-$C_{18}$-fluoroalkyl, preferably $C_1$-$C_6$-fluoroalkyl, more preferably $CF_3$, $CF_2CF_3$ or $CF(CF_3)_2$, most preferably $CF_3$, and $R^1$, $R^2$ and $R^3$ are each as defined above, by reacting compounds of the general formula (VI)

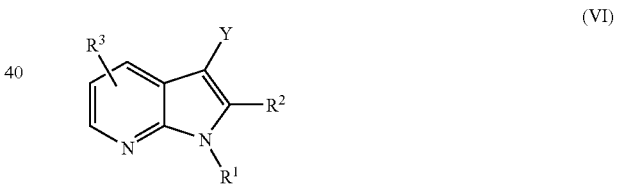
(VI)

in which Y is halogen, preferably I, and $R^1$, $R^2$ and $R^3$ are each as defined above with a fluoroalkylating agent.

In this process, the compounds of the general formula (VI) in which Y is halogen, preferably I, and $R^1$, $R^2$ and $R^3$ are each as defined above are prepared by means of halogenation in a preceding step, for example from compounds of the general formula (II).

In the context of the invention, useful fluoroalkylating agents are, for example, trialkyl(perfluoroalkyl)silanes of the general formula (III)

$(R^4)_3Si(R^F)$ (III)

in which $R^4$ is optionally substituted linear, branched or cyclic $C_1$-$C_{18}$-alkyl, preferably $C_1$-$C_6$-alkyl, and $R^F$ is linear, branched or cyclic $C_1$-$C_{18}$-perfluoroalkyl, preferably $C_1$-$C_6$-perfluoroalkyl, more preferably $CF_3$, $CF_2CF_3$ or $CF(CF_3)_2$, compounds of the general formula (IV)

in which
Y is Br or I and
n is 1 or 2,
or trifluoroacetates of the general formula (V)

in which
M is an alkali metal cation, preferably $Na^+$ or $K^+$, or $C_1$-$C_{18}$-alkyl, preferably $C_1$-$C_6$-alkyl, more preferably methyl.

Preferred fluoroalkylating agents are trifluoromethylating agents. They are preferably those of the general formula (III) in which $R^F$ is $CF_3$, or those of the general formula (IV) or (V).

The process according to the invention is preferably carried out in the presence of fluoride ions. Suitable fluoride ion sources are, for example, alkali metal fluorides or tetraalkylammonium fluorides. For example, these may be potassium fluoride, sodium fluoride, caesium fluoride or tetraalkylammonium fluoride. Particular preference is given to potassium fluoride. The amount of fluoride used may, for example, be 1 to 5 times, preferably 15 to 3 times, based on the amount of X (halogen) to be exchanged in the general formula (I).

The process according to the invention is preferably carried out in the presence of a catalyst. Suitable catalysts are, for example, zinc (for $CF_2Br_2$ as the fluoroalkylating agent), copper (for $CF_2Br_2$ or $CF_3I$ or $CF_3Br$ as a fluoroalkylating agent) or copper(I) salts (for trifluoroacetates of the general formula (V) and trialkyl(perfluoroalkyl)silanes of the general formula (III) as the fluoroalkylating agent). Preference is given to copper(I) salts, particular preference to copper(I) iodide or copper(I) cyanide. The amount of the catalyst used may, for example, be 0.5 to 5 times, preferably 15 to 3 times, based on the amount of X (halogen) to be exchanged in the general formula (I).

The reaction with the fluoroalkylating agent is preferably carried out in the presence of one or more solvent(s), preferably in the presence of one or more aprotic solvent(s), more preferably in the presence of one or more dipolar aprotic solvent(s).

Preferred dipolar aprotic solvents are:
Carboxylic acid derivatives, for example acetonitrile or N,N-dimethylformamide (DMF), N,N-dimethylacetamide (DMAc), N-methylpyrrolidone (NMP) or dimethylimidazolidinone (DMI), sulphones or sulphoxides, for example sulpholane or dimethyl sulphoxide (DMSO), or mixtures of two or more of these solvents. Particular preference is given to N-methylpyrrolidone (NMP), N,N-dimethylformamide (DMF), dimethylimidazolidinone (DMI), N,N-dimethyl-acetamide (DMAc).

The process according to the invention is carried out preferably at temperatures of −10° C. to 150° C., more preferably 0° C. to 100° C., most preferably at 20° C. to 80° C. The reaction time is preferably several hours, more preferably 0.2 to 24 h, most preferably 1 to 18 h.

The performance of the process according to the invention under protective gas atmosphere, for example nitrogen or argon atmosphere, may be advantageous, but is not absolutely necessary.

The process according to the invention may be carried out under standard, elevated or reduced pressure, for example in the range of 0.5 to 5 bar. In general, it is carried out at standard pressure.

The process according to the invention is, for example, carried out in such a way that the compound of the general formula (I) in which X is halogen is initially charged in the appropriate solvent(s) in the presence of a mixture of potassium fluoride and Cu(I) iodide, and the fluoroalkylating agent is metered in and the reaction mixture is stirred at the specified reaction temperature. After the reaction has ended, the reaction mixture is poured onto at least one organic solvent having zero or low miscibility with dipolar aprotic solvents, and optionally extracted repeatedly with the organic solvent(s) having zero or low miscibility with dipolar aprotic solvents. After the solvent(s) has/have been removed, the compound of the general formula (I) can be isolated. To lower the miscibility, water may be added to the dipolar aprotic solvent.

Useful organic solvents having zero or low miscibility with dipolar aprotic solvents, optionally after addition of water, include, for example, ethers, aliphatics or cycloaliphatics. Examples of such organic solvents having zero or low miscibility with dipolar aprotic solvents are methyl tert-butyl ether, hexane, heptane, cyclohexane, methylcyclohekane.

In a preferred embodiment, the compounds of the general formula (VI) in which Y is halogen bear, on the aromatic NH group, a protecting group which may have the definitions specified above for $R^1$ apart from H, preferably an —$SO_2R^x$ or —$C(O)OR^x$ group, in which $R^x$ is optionally substituted $C_1$-$C_{18}$-alkyl, $C_4$-$C_{24}$-aryl or $C_5$-$C_{18}$-arylalkyl, preferably o-, m- or in particular p-toluenesulphonyl or t-butyloxycarbonyl. This protecting group may be removed before or after the reaction with the fluoroalkylating agent. It is also possible to selectively prepare the compounds of the general formula (I) containing this protecting group on the aromatic NH group.

In a further preferred embodiment, the removal of the protecting group from the aromatic NH group and the reaction with the fluoroalkylating agent are effected in one step.

By way of example for the process according to the invention described above, the compounds of the general formula (I) in which X is $CF_3$ may be prepared from compounds of the general formula (II) initially by means of halogenation to compounds of the general formula (VI) in which Y is halogen, and subsequently by reaction with trialkyl(perfluoroalkyl) silanes, preferably trimethyltrifluoromethylsilane, or with trifluoroacetates, preferably sodium trifluoroacetate or potassium trifluoroacetate or methyl trifluoroacetate, in the presence of copper(I) salts, preferably in the presence of copper(I) iodide, and alkali metal fluorides, preferably potassium fluoride or caesium fluoride, and in a dipolar aprotic solvent, for example N-methylpyrrolidone (NMP) or N,N-dimethylformamide (DMF), or by reaction with dibromodifluoromethane in the presence of copper and in a dipolar aprotic solvent, for example N,N-dimethylacetamide (DMAc). It is possible via compounds of the general formula (VI) in which X is Br to prepare compounds of the general formula (I) in which X is $CF_3$ also by reaction with iodotrifluoromethane in the presence of Zn or with bromotrifluoromethane in the presence of TMEDA (tetramethylethylenediamine) and tetraalkylammonium halides, for example ($Bu_4N$)Br (on this subject, cf. M. A. McClinton, Tetrahedron, 1992, 6565-6584).

It is also possible to prepare the inventive compounds of the general formula (I) in which X is $CF_3$ from compounds of the general formula (VI) in which Y is $COR^5$ where $R^5$ is halogen, OH or optionally substituted linear, branched or cyclic $C_1$-$C_{18}$-alkyloxy, preferably $C_1$-$C_6$-alkyloxy, $C_4$-$C_{24}$-aryloxy, preferably $C_6$-$C_{24}$-aryloxy, or $C_5$-$C_{18}$-arylalkyloxy, by reaction with $SF_4$/HF. Such reactions with $SF_4$/HF or DAST/

NaF are described, for example, in Wang C. L. J., Org. React, 34, 319-400 or Hudlicky, M., Org. React. 35, 513-637.

The invention thus further provides a process for preparing the inventive compounds of the general formula (I)

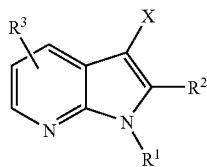

(I)

in which X, $R^1$, $R^2$ and $R^3$ are each as defined above, by reacting compounds of the general formula (VI)

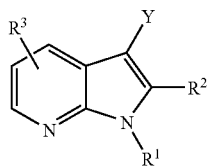

(VI)

in which Y is $COR^5$ where $R^5$ is halogen, OH or optionally substituted linear, branched or cyclic $C_1$-$C_{18}$-alkyloxy, preferably $C_1$-$C_6$-alkyloxy, $C_4$-$C_{24}$-aryloxy, preferably $C_6$-$C_{24}$-aryloxy, or $C_5$-$C_{18}$-arylalkyloxy, and $R^1$, $R^2$ and $R^3$ are each as defined above with $SF_4$ optionally in the presence of HF, or with diethylaminosulphur trifluoride (DAST), optionally in the presence of NaF.

Compounds of the general formula (VI) in which Y is $COR^5$ can be prepared, for example, as described in J. Amer. Chem. Soc. 1956, 78, 1247-1249.

The process according to the invention is preferably carried out in the presence of an excess of HF. The amount of HF may, for example, be 10 to 30 equivalents based on the amount of the compound of the general formula (VI).

The process according to the invention may be carried out in the presence or in the absence of one or more solvent(s). Suitable solvents are, for example, halogenated hydrocarbons, for example dichloromethane.

The process according to the invention may be carried out at standard, elevated or reduced pressure, for example in the range of 0.5 to 5 bar. In general, it is carried out at standard pressure.

The process according to the invention is preferably carried out at temperatures of 80° C. to 140° C. The reaction time is preferably several hours, more preferably 0.2 to 24 h, most preferably 1 to 18 h.

The performance of the process according to the invention under protective gas atmosphere, for example nitrogen or argon atmosphere, may be advantageous, but is not absolutely necessary.

The process according to the invention enables the preparation of the compounds of the general formula (I) under particularly gentle conditions. This allows side reactions, for example dimerizations of compounds of the general formula (VI) in which Y is I, to be substantially suppressed.

The compounds of the general formula (VI)

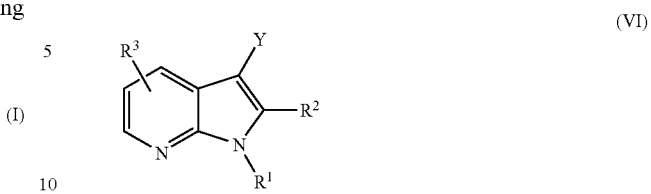

(VI)

in which $R^1$ is H or optionally substituted linear, branched or cyclic $C_1$-$C_{18}$-alkyl, preferably $C_1$-$C_6$-alkyl and $C_3$-$C_6$-cycloalkyl, $C_1$-$C_{18}$-alkoxy, preferably $C_1$-$C_6$-alkoxy, $C_2$-$C_6$-alkenyl, $C_4$-$C_6$-cycloalkenyl, $C_2$-$C_6$-alkynyl, $C_4$-$C_{24}$-aryl, preferably $C_6$-$C_{24}$-aryl, $C_5$-$C_{18}$-arylalkyl, $C_5$-$C_{18}$-aryloxy, $C_5$-$C_{18}$-arylalkoxy, —$SO_2R^x$, —$SO_2NR^xR^y$, —$C(O)OR^x$ or —$C(O)NR^xR^y$, tri-$C_1$-$C_{18}$-alkylsilyl groups and also further suitable NH protecting groups for aromatic compounds, in which $R^x$ and $R^y$ are each independently H or optionally substituted linear, branched or cyclic $C_1$-$C_{18}$-alkyl, preferably $C_1$-$C_6$-alkyl and $C_3$-$C_6$-cycloalkyl, $C_1$-$C_{18}$-alkoxy, preferably $C_1$-$C_6$-alkoxy, $C_2$-$C_6$-alkenyl, $C_4$-$C_6$-cycloalkenyl, $C_2$-$C_6$-alkynyl, $C_4$-$C_{24}$-aryl, preferably $C_6$-$C_{24}$-aryl, $C_5$-$C_{18}$-arylalkyl, $C_5$-$C_{18}$-aryloxy or $C_5$-$C_{18}$-arylalkoxy, $R^2$, $R^3$ are each independently H, Cl, F, Br, $NO_2$, pseudohalogen, formyl or protected formyl, carboxyl, $C(S)NH_2$, $C(O)NH_2$, optionally substituted linear, branched or cyclic $C_1$-$C_{18}$-alkyl, preferably $C_1$-$C_6$-alkyl and $C_3$-$C_6$-cycloalkyl, $C_1$-$C_{18}$-fluoroalkyl, preferably $C_1$-$C_6$-fluoroalkyl, $C_1$-$C_{18}$-alkoxy, preferably $C_1$-$C_6$-alkoxy, $C_1$-$C_{18}$-fluoroalkoxy, preferably $C_1$-$C_6$-fluoroalkoxy, $C_2$-$C_6$-alkenyl, $C_4$-$C_6$-cycloalkenyl, $C_2$-$C_6$-alkynyl, $C_4$-$C_{24}$-aryl, preferably $C_6$-$C_{24}$-aryl, $C_5$-$C_{18}$-arylalkyl or $C_5$-$C_{18}$-arylalkoxy, where, in the case that $R^3$ is $C_5$-$C_{18}$-arylalkyl and it is bonded via the alkyl moiety of the $C_5$-$C_{18}$-arylalkyl radical to the pyridine ring, this alkyl moiety has at least two carbon atoms between aryl moiety of the $C_5$-$C_{18}$-arylalkyl radical and pyridine ring, and Y is halogen or $COR^5$ in which $R^5$ is halogen, OH or optionally substituted linear, branched or cyclic $C_1$-$C_{18}$-alkyloxy, preferably $C_1$-$C_6$-alkyloxy, $C_4$-$C_{24}$-aryloxy, preferably $C_6$-$C_{24}$-aryloxy or $C_5$-$C_{18}$-arylalkyloxy, where at least one, preferably at least two, of the $R^1$, $R^2$ or $R^3$ radicals is not H have to date not been described in the literature and therefore likewise form part of the subject-matter of the present invention.

In a preferred embodiment, $R^1$ in the inventive compounds of the general formula (VI) is not H. In these inventive compounds, $R^1$ is more preferably —$SO_2R^x$, —$SO_2NR^xR^y$, —$C(O)OR^x$, or —$C(O)NR^xR^y$, where $R^x$ and $R^y$ are each independently H or optionally substituted $C_1$-$C_{18}$-alkyl, $C_4$-$C_{24}$-aryl or $C_5$-$C_{18}$-arylalkyl, preferably —$SO_2R^x$ or —$C(O)OR^x$, more preferably o-, m- or in particular p-toluenesulphonyl or t-butyloxycarbonyl.

Examples of inventive compounds of the general formula (VI) are, for example, the following compounds of the formulae (VI-1) and (VI-2):

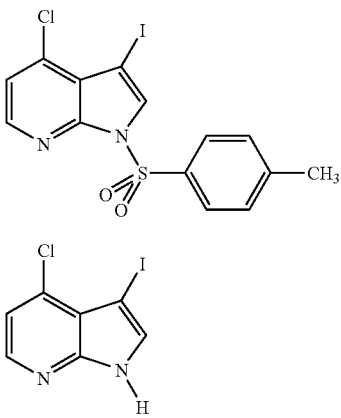

The inventive compounds of the general formula (VI) are outstandingly suitable for preparing the compounds of the general formula (I), in particular with the above-described process according to the invention.

The inventive compounds of the general formula (I) are suitable, for example, as intermediates for the preparation of active pharmaceutical ingredients or have pharmaceutical activity themselves and are suitable as active pharmaceutical ingredients. The active pharmaceutical ingredients prepared from the inventive compounds of the general formula (I) or the inventive compounds of the general formula (I) themselves may be superior to the known compounds, for example, with regard to solubility, efficacy or pharmacokinetics.

The examples which follow serve to illustrate the invention by way of example and are not to be interpreted as a restriction.

EXAMPLES

1.) Preparation of 4-chloro-3-iodo-1H-pyrrolo[2,3-b]pyridine (VI-2)

250 g (1.64 mol) of 4-chloro-1H-pyrrolo[2,3-b]pyridine were initially charged together with 328 g (5.85 mol) of pulverulent KOH in 3000 ml of DMF and cooled to 0° C. A solution of 416 g (1.64 mol) of iodine in 3000 ml of DMF was added dropwise with cooling to this suspension and, on completion of addition, the suspension was stirred at 0° C. for a further 4 h. On completion of the reaction, the mixture was added to ice-water with stirring, and the solid formed was filtered off with suction and subsequently dried under high vacuum. A total of 403 g (1.45 mol, 88%) of 4-chloro-3-iodo-1H-pyrrolo[2,3-b]pyridine were isolated as a colourless solid.

1H NMR (DMSO): 7.21 (d, 1H, H-arom), 7.81 (d, 1H, H-arom), 8.19 (d, 1H, H-arom), 12.45 (br, s, 1H, N—H).

LC-MS: 278 [M+]

2.) Preparation of 4-chloro-1-(toluene-4-sulphonyl)-3-iodo-1H-pyrrolo[2,3-b]pyridine (VI-1)

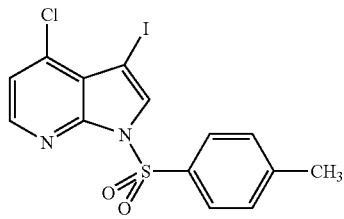

Under protective gas atmosphere (argon), 63.5 g (1.59 mol) of sodium hydride were suspended in 1000 ml of abs. THF. To this were added dropwise with cooling at a temperature of 0-5° C. a solution of 402 g (1.44 mol) of 4-chloro-3-iodo-1H-pyrrolo[2,3-b]pyridine in 3000 ml of abs. THF, and the reaction mixture was left to stir for a further 15 minutes after completion of addition. Subsequently, 358 g (1.88 mol) of p-toluenesulphonyl chloride were added in portions to the reaction mixture in such a way that the temperature was kept between 5-10° C. After the addition had ended, the mixture was allowed to come to 20° C. and stirred at this temperature for a further hour. On completion of conversion (TLC monitoring of conversion), the reaction mixture was admixed with 20 l of saturated $NaHCO_3$ solution and 10 l of ethyl acetate, and extracted, and the organic phase was removed. The aqueous phase was extracted twice more with 10 l each time of ethyl acetate, and the organic phases were combined, dried and freed of volatile constituents in a water-jet vacuum. To purify the crystalline crude product, it was taken up in dichloromethane and chromatographed using silica gel ($CH_2Cl_2$: 40/60 petroleum ether=3:7). After the solvents had been removed, the crystal slurry was extractively stirred in diethyl ether, and the solids were filtered off with suction and dried at 20° C. under high vacuum. A total of 372 g (0.86 mol, 60%) of 4-chloro-1-(toluene-4-sulphonyl)-3-iodo-1H-pyrrolo[2,3-b]pyridine were isolated as a colourless solid.

1H NMR (DMSO): 2.35 (s, 3H, —$CH_3$), 7.44 (d, 2H, H-arom), 7.46 (d, 1H, H-arom), 8.02 (d, 2H, H-arom), 8.23 (s, 1H, H-arom), 8.34 (d, 1H, H-arom).

LC-MS: 432 [M+]

3.) Preparation of 4-chloro-1-(toluene-4-sulphonyl)-3-trifluoromethyl-1H-pyrrolo[2,3-b]pyridine (1-4)

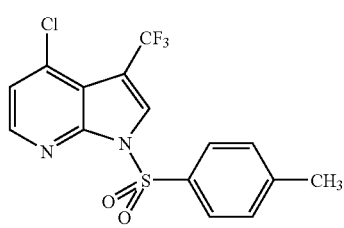

Under protective gas atmosphere (argon), 23.1 g (0.398 mol) of dry potassium fluoride and 75.7 g (0.398 mol) of copper(I) iodide were titrated together and heated to 220° C. under high vacuum with agitation for 10 minutes until a slightly greenish colouration appeared. A reaction flask was initially charged under protective gas atmosphere (argon) with the calcined mixture of potassium fluoride and copper(I) iodide together with 170 ml of absolute NMP and 170 ml of absolute DMF, and 86 g (0.199 mol) of 4-chloro-1-(toluene-4-sulphonyl)-3-iodo-1H-pyrrolo[2,3-b]pyridine were subsequently introduced in portions at 20° C. with stirring to form a light grey suspension. 62.1 g (0.437 mol) of trimethyltrifluoromethylsilane were added dropwise to the reaction mixture within 20 minutes and the mixture was left to stir at 20° C. for 18 h. On completion of conversion (GC monitoring of conversion), the reaction mixture was added to 2000 ml of methyl tert-butyl ether, the organic phase was decanted and the residue was dispersed once more with 1000 ml of methyl tert-butyl ether. The combined organic phases were washed three times with 2000 ml each time of water and subsequently dried over $MgSO_4$. Filtration and removal of the volatile constituents in a water-jet vacuum resulted in 50.1 g (0.134 mol; 67%) of 4-chloro-1-(toluene-4-sulphonyl)-3-trifluoromethyl-1H-pyrrolo[2,3-b]pyridine as a beige solid.

1H NMR (DMSO): 2.37 (s, 3H, —$CH_3$), 7.48 (d, 2H, H-arom), 7.62 (d, 1H, H-arom), 8.12 (d, 2H, H-arom), 8.47 (d, 1H, H-arom), 8.67 (s, 1H, H-arom).

LC-MS: 374 [M+]

4.) Preparation of 4-chloro-3-trifluoromethyl-1H-pyrrolo[2,3-b]pyridine (I-2)

(I-2)

52.3 g (200 mmol) of tetra-n-butylammonium fluoride are added to a solution of 30 g (80.0 mmol) of 4-chloro-1-(toluene-4-sulphonyl)-3-trifluoromethyl-1H-pyrrolo[2,3-b]pyridine in 250 ml of absolute THF and the mixture is stirred at 20° C. for 20 minutes. On completion of conversion (TLC monitoring), the mixture is admixed with 300 ml of saturated $NaHCO_3$ solution and subsequently extracted three times with 500 ml each time of ethyl acetate. The combined organic phases are washed with saturated NaCl solution, dried over $MgSO_4$ and freed of volatile constituents in a water-jet vacuum. Purification of the crystalline crude product by chromatography through silica gel ($CH_2Cl_2$: MeOH=30:1) results in 13.1 g (59.5 mmol; 74%) of 4-chloro-3-trifluoromethyl-1H-pyrrolo[2,3-b]pyridine as a beige solid.

1H NMR (DMSO): 7.40 (d, 1H, H-arom), 8.28 (s, 1H, H-arom), 8.34 (d, 1H, H-arom), 12.88 (br, s, 1H, N—H).

LC-MS: 220 [M+]

What is claimed is:

1. The compound of the formula (I)

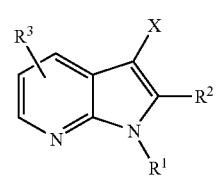

(I)

in which $R^1$ is H or optionally substituted linear, branched or cyclic $C_1$-$C_{18}$-alkyl, $C_1$-$C_{18}$-alkoxy, $C_2$-$C_6$-alkenyl, $C_4$-$C_6$-cycloalkenyl, $C_2$-$C_6$-alkynyl, $C_4$-$C_{24}$-aryl, $C_5$-$C_{18}$-arylalkyl, $C_5$-$C_{18}$-aryloxy, $C_5$-$C_{18}$-arylalkoxy, —$SO_2R^x$, —$SO_2NR^xR^y$, —C(O)$OR^x$, —C(O)$NR^xR^y$ or tri-$C_1$-$C_{18}$-alkylsilyl groups, in which $R^x$ and $R^y$ are each independently H or optionally substituted linear, branched or cyclic $C_1$-$C_{18}$-alkyl, $C_1$-$C_{18}$-alkoxy, $C_2$-$C_6$-alkenyl, C4-$C_6$-cycloalkenyl, $C_2$-$C_6$-alkynyl, $C_4$-$C_{24}$-aryl, $C_5$-$C_{18}$-arylalkyl, $C_5$-$C_{18}$-aryloxy or $C_5$-$C_{18}$-arylalkoxy, $R^2$, $R^3$ are each independently H, Cl, F, Br, $NO_2$, pseudohalogen, formyl or protected formyl, carboxyl, C(S)$NH_2$, C(O)$NH_2$, optionally substituted linear, branched or cyclic $C_1$-$C_{18}$-alkyl, $C_1$-$C_{18}$-fluoroalkyl, $C_1$-$C_{18}$-alkoxy, $C_1$-$C_{18}$-fluoroalkoxy, $C_2$-$C_6$-alkenyl, $C_4$-$C_6$-cycloalkenyl, $C_2$-$C_6$-alkynyl, $C_4$-$C_{24}$-aryl, $C_5$-$C_{18}$arylalkyl or $C_5$-$C_{18}$-arylalkoxy, where, in the case that $R^3$ is $C_5$-$C_{18}$-arylalkyl and it is bonded via the alkyl moiety of the $C_5$-$C_{18}$-arylalkyl radical to the pyridine ring, this alkyl moiety has at least two carbon atoms between aryl moiety of the $C_5$-$C_{18}$-arylalkyl radical and pyridine ring, and X is $C_1$-$C_{18}$-fluoroalkyl, or a salt of the compounds of the general formula (I).

2. The compound according to claim 1, wherein $R^1$ is H or —$SO_2R^x$ or —C(O)$OR^x$, in which $R^x$ is optionally substituted $C_1$-$C_{18}$-alkyl, $C_4$-$C_{24}$-aryl or $C_5$-$C_{18}$-arylalkyl.

3. The compound according to claim 1, wherein $R^2$ is H or $C_1$-$C_6$-alkyl, $C_6$-$C_{24}$-aryl or $C_5$-$C_{18}$-arylalkyl.

4. The compound according to Claim 1 wherein $R^3$ is H, Cl, F, Br, $NO_2$, CN, formyl or protected formyl, $C_1$-$C_6$-alkyl, $C_1$-$C_6$-fluoroalkyl, $C_1$-$C_6$-alkoxy, $C_1$-$C_6$-fluoroalkoxy, $C_6$-$C_{24}$-aryl, $C_5$-$C_{18}$-arylalkyl, $C_5$-$C_{18}$arylalkoxy.

5. The compound according to claim 1, wherein X is $C_1$-$C_6$fluoroalkyl.

6. A mixture comprising compounds according to claim 1, wherein the mixture comprises compunds wherein $R^2$ and $R^3$ are identical and wherein for at least one compound $R^1$ is H and wherein for at least one compound $R^1$ is a protection group.

7. A process for preparing compounds of the general formula (I)

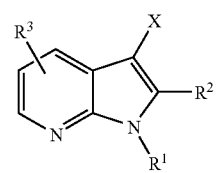

(I)

in which
- $R^1$ is H or optionally substituted linear, branched or cyclic $C_1$-$C_{18}$-alkyl, $C_1$-$C_{18}$-alkoxy, $C_2$-$C_6$-alkenyl, $C_4$-$C_6$-cycloalkenyl, $C_2$-$C_6$-alkynyl, $C_4$-$C_{24}$-aryl, $C_5$-$C_{18}$-arylalkyl, $C_5$-$C_{18}$-aryloxy, $C_5$-$C_{18}$-arylalkoxy, —$SO_2R^x$, —$SO_2NR^xR^y$, —$C(O)OR^x$, —$C(O)NR^xR^y$ or tri-$C_1$-$C_{18}$-alkylsilyl groups,
  - in which $R^x$ and $R^y$ are each independently H or optionally substituted linear, branched or cyclic $C_1$-$C_{18}$-alkyl, $C_1$-$C_{18}$-alkoxy, $C_2$-$C_6$-alkenyl, $C_4$-$C_6$-cycloalkenyl, $C_2$-$C_6$-alkynyl, $C_4$-$C_{24}$-aryl, $C_5$-$C_{18}$-arylalkyl, $C_5$-$C_{18}$-aryloxy or $C_5$-$C_{18}$-arylalkoxy,
- $R^2$, $R^3$ are each independently H, Cl, F, Br, $NO_2$, pseudohalogen, formyl or protected formyl, carboxyl, $C(S)NH_2$, $C(O)NH_2$, optionally substituted linear, branched or cyclic $C_1$-$C_{18}$-alkyl, $C_1$-$C_{18}$-fluoroalkyl, $C_1C_{18}$-alkoxy, $C_1$-$C_{18}$-fluoroalkoxy, $C_2$-$C_6$-alkenyl, $C_4$-$C_6$-cycloalkenyl, $C_2$-$C_6$-alkynyl, $C_4$-$C_{24}$aryl, $C_5$-$C_{18}$ arylalkyl or $C_5$-$C_{18}$-arylalkoxy, where, in the case that $R^3$ is $C_5$-$C_{18}$-arylalkyl and it is bonded via the alkyl moiety of the $C_5$-$C_{18}$-arylalkyl radical to the pyridine ring, this alkyl moiety has at least two carbon atoms between aryl moiety of the $C_5$-$C_{18}$-arylalkyl radical and pyridine ring, and
- X is $C_1$-$C_{18}$-fluoroalkyl, comprising reacting compounds of formula (VI)

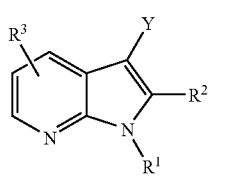

(VI)

in which Y is halogen, and $R^1$, $R^2$ and $R^3$ are each as defined above,
with a fluoroalkylating agent.

8. The process according to claim 7, wherein X is $CF_3$ and the fluoroalkylating agent is a trifluoromethylating agent.

9. The process according to claim 7, wherein the reaction is carried out in the presence of one or more solvent(s).

10. The process according to claim 7, wherein the compounds of the general formula (I) are prepared in the presence of fluoride ions.

11. The process according to claim 7, wherein the compounds of the general formula (I) are prepared in the presence of a catalyst.

12. The process according to claim 7, wherein the compound of the general formula (I) in which $R^1$ is H, after the reaction with the fluoroalkylating agent, are prepared from compounds of the general formula (VI) in which $R^1$ in formula (VI) is —$SO_2R^x$ or —$C(O)OR^x$, in which $R^x$ is optionally substituted $C_1$-$C_{18}$-alkyl, $C_4$-$C_{24}$-aryl or $C_5$-$C_{18}$-arylalkyl.

13. A process for preparing compounds of the general formula (I)

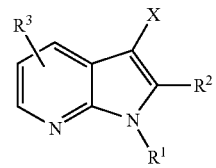

(I)

in which
- $R^1$ is H or optionally substituted linear, branched or cyclic $C_1$-$C_{18}$-alkyl, $C_1$-$C_{18}$-alkoxy, $C_2$-$C_6$-alkenyl, $C_4$-$C_6$-cycloalkenyl, $C_2$-$C_6$-alkynyl, $C_4$-$C_{24}$-aryl, $C_5$-$C_{18}$-arylalkyl, $C_5$-$C_{18}$-aryloxy, $C_5$-$C_{18}$-arylalkoxy, —$SO_2R^x$, —$SO_2NR^xR^y$, —$C(O)OR^x$, —$C(O)NR^xR^y$ or tri-$C_1$-$C_{18}$-alkylsilyl groups,
  - in which $R^x$ and $R^y$ are each independently H or optionally substituted linear, branched or cyclic $C_1$-$C_{18}$-alkyl, $C_1$-$C_{18}$-alkoxy, $C_2$-$C_6$-alkenyl, $C_4$-$C_6$-cycloalkenyl, $C_2$-$C_6$-alkynyl, $C_4$-$C_{24}$-aryl, $C_5$-$C_{18}$-arylalkyl, $C_5$-$C_{18}$-aryloxy or $C_5$-$C_{18}$-arylalkoxy,
- $R^2$, $R^3$ are each independently H, Cl, F, Br, $NO_2$, pseudohalogen, formyl or protected formyl, carboxyl, $C(S)NH_2$, $C(O)NH_2$, optionally substituted linear, branched or cyclic $C_1$-$C_{18}$-alkyl, $C_1$-$C_{18}$-fluoroalkyl, $C_1$-$C_{18}$-alkoxy, $C_1$-$C_{18}$-fluoroalkoxy, $C_2$-$C_6$-alkenyl, $C_4$-$C_6$-cycloalkenyl, $C_2$-$C_6$-alkynyl, $C_4$-$C_{24}$-aryl, $C_5$-$C_{18}$arylalkyl or $C_5$-$C_{18}$-arylalkoxy, where, in the case that $R^3$ is $C_5$-$C_{18}$-arylalkyl and it is bonded via the alkyl moiety of the $C_5$-$C_{18}$-arylalkyl radical to the pyridine ring, this alkyl moiety has at least two carbon atoms between aryl moiety of the $C_5$-$C_{18}$arylalkyl radical and pyridine ring, and
- X is $C_1C_{18}$fluoroalkyl, comprising reacting compounds of formula (VI)

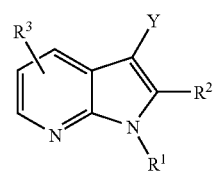

(VI)

in which
- Y is $COR^5$ in which $R^5$ is halogen, OH or optionally substituted linear, branched or cyclic $C_1$-$C_{18}$-alkyloxy, and
- $R^1$, $R^2$ and $R^3$ are each as defined above, with $SF_4$, optionally in the presence of HF.

* * * * *